United States Patent
Iske et al.

(10) Patent No.: US 6,949,109 B2
(45) Date of Patent: Sep. 27, 2005

(54) SPRING-ACTUATED, RETRACTABLE-BLADED SURGICAL SCALPEL

(75) Inventors: Mark L. Iske, Missouri City, TX (US); Timothy C. Thompson, Los Alamos, NM (US); Charles T. Gregg, Los Alamos, NM (US)

(73) Assignee: Innovative Surgical Technology, Inc., Los Alamos, NM (US)

( * ) Notice: Subject to any disclaimer, the term of this patent is extended or adjusted under 35 U.S.C. 154(b) by 95 days.

(21) Appl. No.: 10/646,968

(22) Filed: Aug. 22, 2003

(65) Prior Publication Data

US 2004/0111106 A1 Jun. 10, 2004

Related U.S. Application Data

(60) Provisional application No. 60/405,442, filed on Aug. 23, 2002.

(51) Int. Cl.$^7$ .............................................. A61B 17/32
(52) U.S. Cl. ...................................... 606/167; 30/162
(58) Field of Search ................................. 606/162, 166, 606/167; 30/62, 162, 151, 164, 167, 335

(56) References Cited

U.S. PATENT DOCUMENTS

| | | | | |
|---|---|---|---|---|
| 5,403,337 A | * | 4/1995 | Platts | 606/167 |
| 5,431,672 A | * | 7/1995 | Cote et al. | 606/167 |
| 6,589,258 B2 | * | 7/2003 | Pilo et al. | 606/167 |
| 6,645,216 B2 | * | 11/2003 | Masury et al. | 606/167 |

* cited by examiner

Primary Examiner—(Jackie) Tan-Uyen T. Ho
(74) Attorney, Agent, or Firm—Samuel M. Freund; Cochran Freund & Young LLC

(57) ABSTRACT

A surgical scalpel having a replaceable, spring-actuated, retractable cutting blade which may be locked in the operating or deployed position and returned to its safety position using a single digit on one hand.

18 Claims, 4 Drawing Sheets

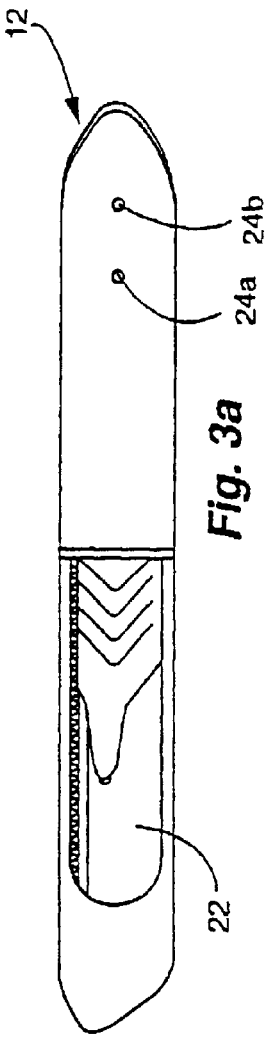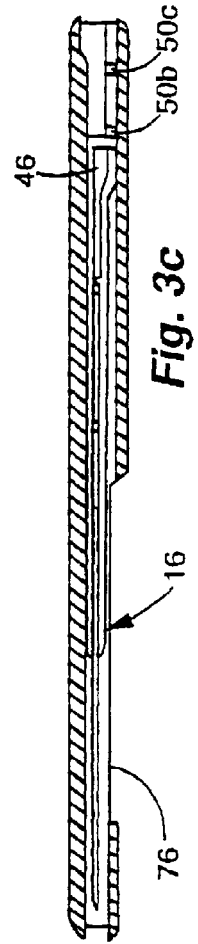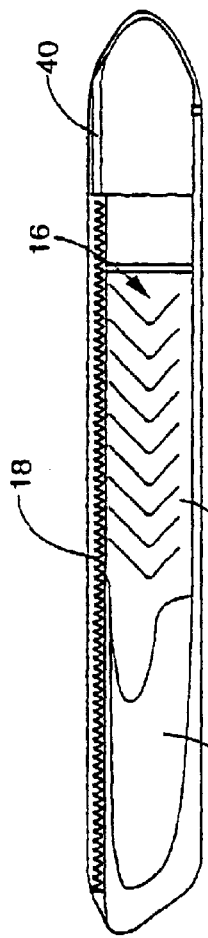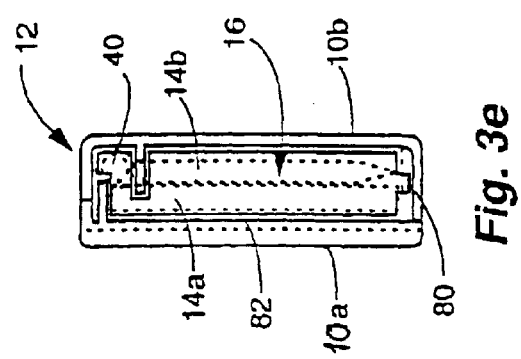

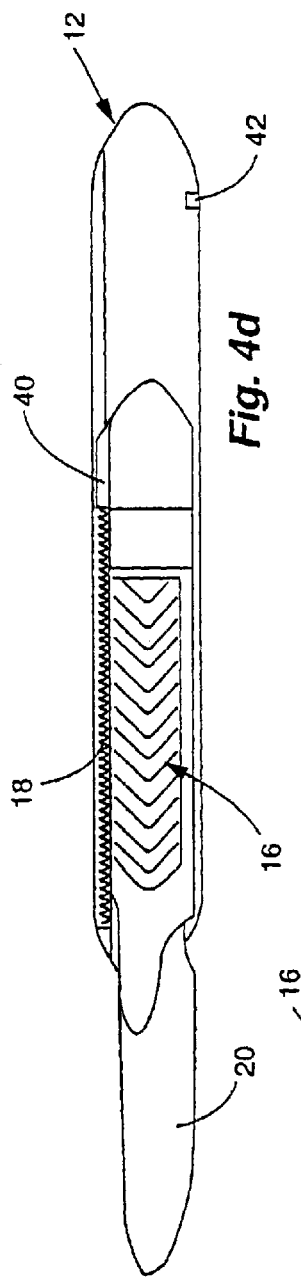
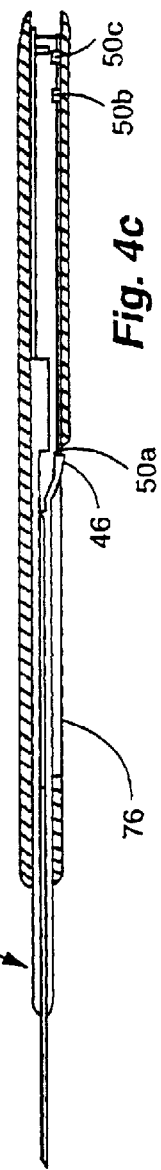
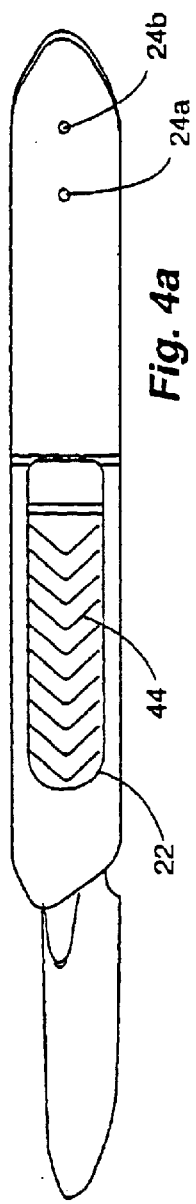

SPRING-ACTUATED, RETRACTABLE-BLADED SURGICAL SCALPEL

CROSS REFERENCE TO RELATED APPLICATIONS

The present application is based upon and claims the benefit of U.S. Provisional Patent Application Ser. No. 60/405,442 by Mark L. Iske, et al. entitled "Spring-Actuated, Retractable-Bladed Surgical Scalpel" filed Aug. 23, 2002, the entire contents of which is hereby specifically incorporated by reference for all it discloses and teaches.

FIELD OF THE INVENTION

The present invention relates generally to surgical cutting instruments and, more particularly, to surgical scalpels having spring-actuated retractable blades.

BACKGROUND OF THE INVENTION

It is well known that existing surgical cutting implements provide a significant potential for harm to surgeons and support personnel. That is, with attention directed toward the patient, rapid handling of surgical instruments having exposed sharp edges occasionally leads to cuts and puncture wounds with loss of integrity of surgical gloves, thereby increasing the risk of life-threatening infectious diseases.

In U.S. Pat. No. 5,403,337 for "Retractable-Bladed Surgical Scalpel" which issued to David Platts on Apr. 4, 1995, a spring-actuated retractable-bladed scalpel having interchangeable blades is described. Shipping and use of this instrument has identified three difficulties. First, if the package containing the scalpel is dropped, there is a likelihood that the cutting edge will pierce the sterile package within which it is located. Moreover, only a limited number of scalpel blades can be used with the single-size slide member, and the slide moves with difficulty within the channel in the handle if the size of the scalpel is increased to accommodate additional blade sizes.

The Saf-T-Pass Retractable Scalpel, a recently marketed product from Surgical Specialties Corporation, minimizes the risk of scalpel injury by providing a surgical scalpel having a blade which is deployed when a locking button disposed on the scalpel's slide and moving therewith is pushed forward relative to the scalpel's handle by a user of the scalpel. A final action of rotating the locking button secures the slide which holds the blade in the open position. The blade is retracted when the locking button is rotated in the reverse direction by the user and the slide is permitted to move under the action of a spring thereon, thereby shielding the blade within the handle in which it originally was situated. A movable slide cover prevents the slide from being moved forward until the slide cover is drawn rearward by the user, rendering the deployment of the surgical blade a two-step process.

Accordingly, it is an object of the present invention to provide a retractable-bladed surgical scalpel where accidental piercing of the sterilized packaging is prevented when packaged scalpels are dropped or otherwise roughly handled.

Another object of the present invention is to provide a retractable-bladed surgical scalpel which can accept a plurality of popular scalpel blades.

Still another object of the invention is to provide a retractable-bladed surgical scalpel having smooth motion for deployment and retraction of the cutting blade.

Yet another object of the invention is to provide a retractable-bladed surgical scalpel for which the cutting blade may be deployed by a single motion by the user.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein the surgical scalpel having a spring-actuated retractable blade hereof includes: an elongated handle having a first side and a second side, a first elongated cavity within the handle extending over the long dimension thereof and opening to the outside at both a forward end and a rearward end, the first side having an elongated window therethrough along the long dimension of the handle and located toward the forward end thereof and a second window therethrough disposed toward the rearward end of the handle, the first side further having a first tab extending into the first cavity and located in the vicinity of the edge of the elongated window closest to the rearward end of the handle and a second tab extending into the first cavity between the second window and the rearward end of the handle; the second side having an interior elongated slot therein which terminates before reaching the forward end of the handle and which opens to the outside of the handle at the rearward end thereof; a cutting blade; an elongated slide having a first end and a second end adapted to slidably move longitudinally through the first cavity in the handle and to receive the cutting blade in the region of the first end thereof; a portion adapted to be engaged by and actuated by a digit through the elongated window; a raised, deformable latch in the region of the second end on the side thereof of the digit-engaging portion for engaging either of the first or second tabs in the handle; and a tab adapted to move within the slot in the second side of the handle; means for engaging and reversibly immobilizing the slide when the slide is located in its rearwardmost position in the handle; and means for providing a force on the slide directed toward the rearward end of the handle.

Benefits and advantages of the present retractable-bladed scalpel include a scalpel which can readily accept a plurality of popular scalpel blades and which maintains smooth motion in the deployment of the cutting blade independent of the size of the blade, where the cutting blade may be deployed by a single motion of the movable slide by the user, and where accidental piercing of the sterilized packaging containing the scalpel is avoided when the packaging is dropped or otherwise roughly handled.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIGS. 3a–3e show cross sectional views of the scalpel of the present invention in its retracted configuration.

FIGS. 4a–4d show cross sectional views of the scalpel of the present invention in its deployed configuration.

DETAILED DESCRIPTION

Briefly, the present invention includes a surgical scalpel having a retractable blade which may be locked in the operating or deployed configuration using a single digit on one hand. Improvements over existing retractable-bladed surgical scalpels include a device for reducing the likelihood that a packaged and sterilized blade can pierce the sterilization envelope as a result of rough handling of the package, a handle which is capable of receiving several sizes of slides bearing cutting blades, and a handle in which the slide contact with the handle is minimized, thereby providing smoother operation of the surgical scalpel.

Figure 1:
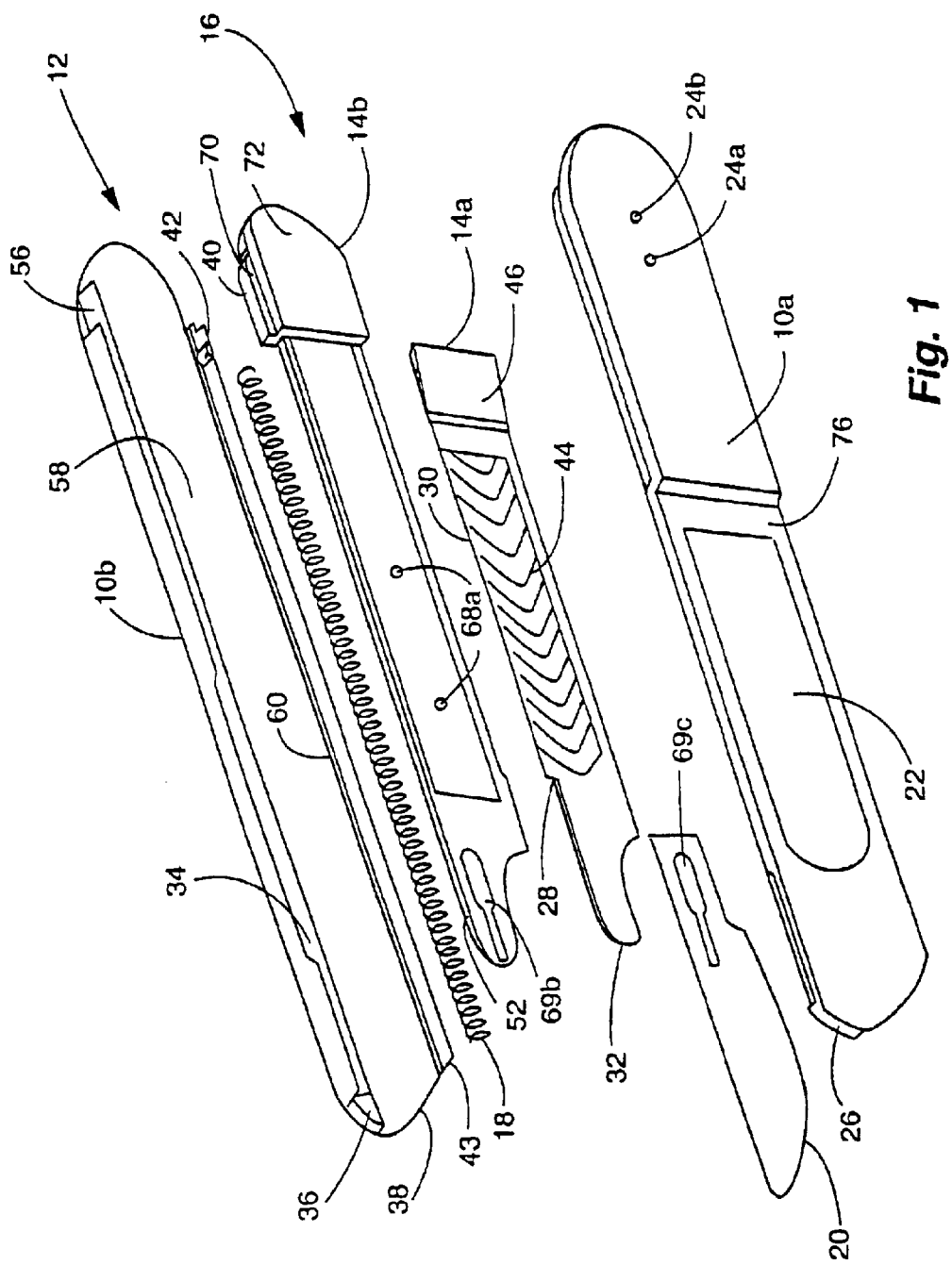
FIG. 1 is a projection view of the parts of the scalpel of the present invention showing the two sides of the handle, the two parts of the slide, a coil spring, and a blade.

Reference will now be made in detail to the present preferred embodiments of the invention, examples of which are illustrated in the accompanying drawings. Identical or similar structure is identified by the same callouts. Turning now to FIG. 1, an exploded projection view of the pieces of the present retractable-bladed scalpel is shown illustrating, in particular, the two sides, 10a and 10b, which comprise handle, 12, the two slide halves, 14a and 14b which comprise slide, 16, means for imparting a rearward restoring force to slide 16, such as a coil spring or a resilient deformable material capable of performing this function, 18, and cutting blade, 20. Sides 10a and 10b, when brought together, form a cavity in which slide 16 is slidably disposed. Three windows are also illustrated in side 10a of handle 12: elongated window, 22, and small windows, 24a and 24b. Tab, 26, for engaging slide 16 at the location of the termination, 28, of raised portion, 30, in the forward end, 32, thereof when slide 16 is in its deployed position.

FIG. 1 also illustrates channel, 34, having stop 36 in the forward end, 38, thereof in side 10b of handle 12 in which coil spring 18 is disposed, tab, 40, disposed on side 14b of slide 16 for engaging coil spring 18 and tab, 42, formed on lower flange, 43, of side 10b of handle 12 for securing slide 16 in its retracted position. Digit-engaging portion, 44, of slide half 14a of slide 16 and deformable latch 46 thereon are also illustrated and will be elaborated upon hereinbelow.

Figure 2:
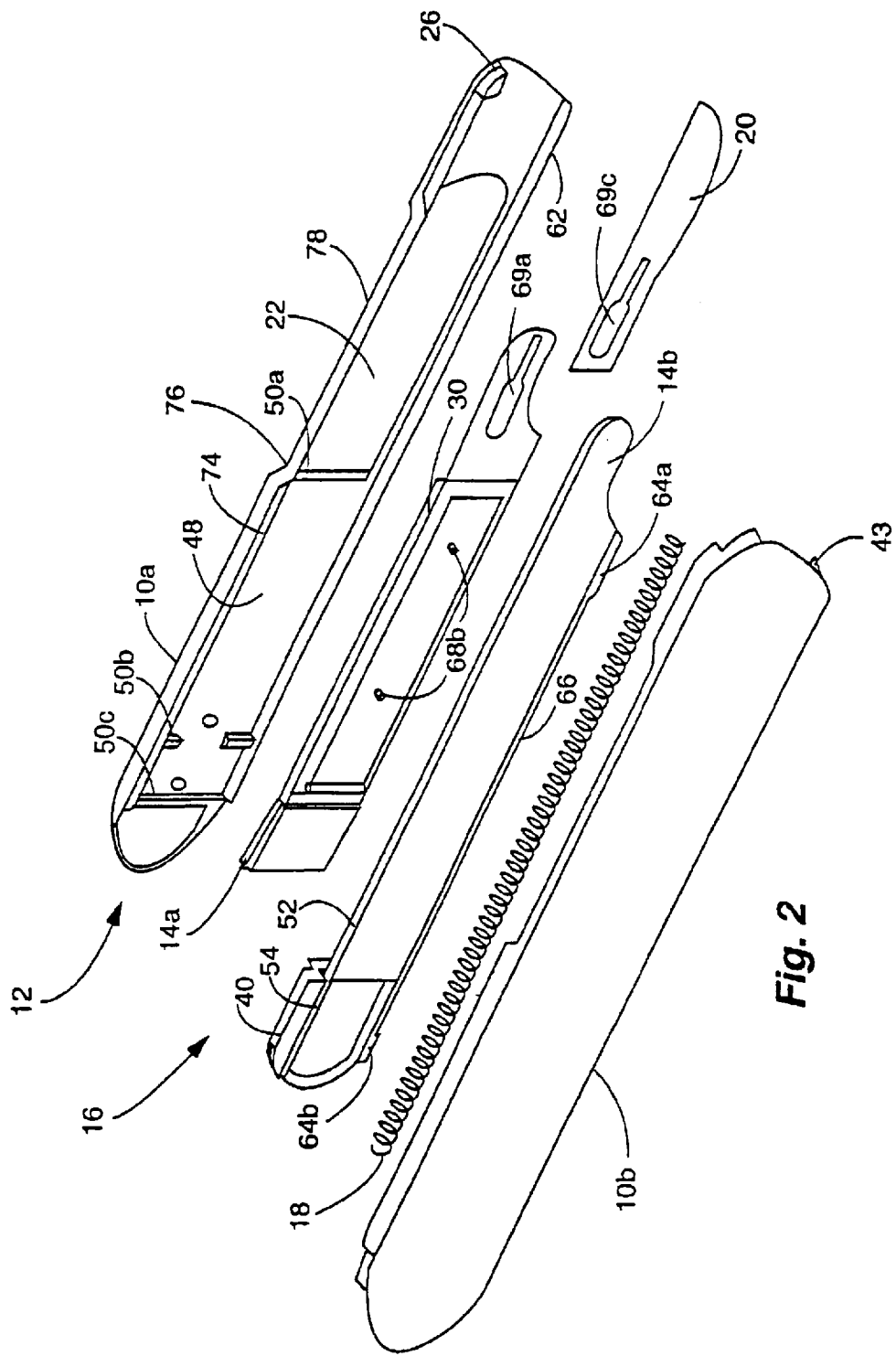
FIG. 2 is a projection view of the other side of the scalpel of the present invention shown in FIG. 1 hereof showing the two sides of the handle, the two parts of the slide, a coil spring, and a blade.

FIG. 2 shows an exploded projection view of the retractable-bladed scalpel shown in FIG. 1 hereof from the other side thereof. Of note in the inside, 48, of side 10a of handle 12, three 3 tabs or projections are illustrated, 50a, 50b, and 50c, the purpose of which will be explained in detail hereinbelow. Tab 40 and the top edge, 52, of slide half 14b form slot, 54, which is adapted to slidably engage the lower defining portion, 56, (FIG. 1) of channel 34 on the inside, 58, of side 10b. Raised portion, 60, (FIG. 1) and flange, 62, of side 10a of handle 12 cooperate to form a channel which slidably engages tabs, 64a and 64b, of lower portion, 66, of slide half 14b of slide 16.

Depressions, 68a, in slide half 14b shown in FIG. 1 are adapted to receive posts, 68b, in slide half 14a shown in FIG. 2 for joining the two slide halves together.

Matching raised portion, 69a, and depression, 69b, capture cutout, 69c, in blade 20 when the two slide halves are joined, thereby affixing blade 20 to slide 16. It should be mentioned that blade 20 may be removed from slide 16 for replacement. Further, notch, 70, in end piece, 72, of slide half 14b of slide 16 is adapted to slidably engage flange, 74, in side 10a of handle 12, thereby guiding tab 40 which is also formed in end piece 72, in channel 34. A portion, 76, of the outside, 78, of side 10a is cut away to permit easier access to digit-engaging portion 44 through window 22.

FIG. 3a shows a schematic representation of the side view of the assembled scalpel of the present invention with the surgical blade in its retracted position, while FIG. 3b shows the top view thereof. Elongated window 22 and smaller windows 24a and 24b are shown in handle 12. FIG. 3c shows a schematic representation of the same view as shown in FIG. 3b, except that the top of handle 12 is removed and slide 16 is visible. FIG. 3d is a schematic representation of the same view as that shown in FIG. 3a except that side 10a has been removed to expose slide 16. In particular, digit-engaging portion 44 is clearly visible on slide 16 as is spring 18 and blade 20.

FIG. 3e shows a schematic representation of the rear view of the present scalpel showing, in particular, the channel, 80, formed the cooperation of raised portion, 60, (FIG. 1) with flange, 62, of side 10a of handle 12 which slidably engages tabs, 64a and 64b, of lower portion, 66, of slide half 14b of slide 16 (all shown in FIG. 2), and cavity, 82, which is formed by sides 10a and 10b of handle 12.

FIGS. 4a–4d show the same views as FIGS. 3a–3d, respectively, except that the knife is in its extended or deployed condition. Of note is that FIG. 4c illustrates the latching action of deformable latch 46 in slide half 14a in contact with tab 50a which secures stop 28 of slide 16 against tab 26 in handle 12 when slide 16 is in its fully forward position. Although handle 12 and slide 16 are fabricated as handle halves 10a and 10b and slide halves 14a and 14b, respectively, the halves are glued or welded together by any of several well-known joining processes as part of the assembly process for the knife.

The retractable knife of the present invention is packaged for shipment with slide 16 is in its rearward or undeployed position, whereby tab 42 wedges slide 16 firmly within handle cavity 82 (FIG. 3e). This prevents slide 16 from readily moving forward such that blade 20 can puncture a sterilization envelope if the knife is accidentally dropped. In actual operation, latch 46 is may engage any of tabs 50a, 50b or 50c, while being deformable such that slide 16 can slide through handle cavity 82 under the action of either coil spring 18 or a digit, generally a thumb, in contact with digit-engaging portion 44. Spring 18 forces latch 46 against whichever of the tabs the latch member is located in forward of it when no external force is applied to digit-engaging portion 44 of slide 16.

As stated hereinabove, handle 12 is relieved 76 in the region of window 22 to provide better access to digit-engaging portion 44 and latch 46. The shape of relieved portion 76 is chosen such that an operator may readily engage digit-engaging portion 44 of slide 16 in order to deploy blade 20, while making it more difficult to depress latch 46 until it is desired to retract the blade. Therefore, latch 46 cannot easily be accidentally released by the operator during use of the instrument. Additionally, latch 46 may slightly extend through the rear portion of window 22 when slide 16 is fully deployed to more positively secure slide 16 in its forwardmost position, without affecting the scalpel's resistance to accidental retraction of slide 16.

FIG. 3c illustrates latch 44 engaging tab 50b under the action of spring 18 such that the knife is in its closed or retracted position. Given the length of slide 16, this position would be attained by a user first overcoming the wedging action of tab 42 and moving slide 16 sufficiently far forward using digit-engaging portion 44 of slide 16 such that latch 46 is moved forward of tab 50b and allowed to be returned thereto under the action of spring 18. Depressing deformable latch 46 by inserting a solid object through window 24a will allow slide 16 to move rearward and engage tab 50c, again under the action of spring 18. By depressing latch 46 once more, but through window 24b, slide 16 will move rearward and out of cavity 82 under the action of spring 18, at which time slide 16 can be removed from handle 12 in order to exchange slides. Tab 50c and window 24b together permit longer slides accommodating blades 20 having different sizes and shapes to be used.

As described hereinabove, FIG. 4c illustrates the latching action of deformable latch 46 in slide half 14a in contact with tab 50a which secures stop 28 of slide 16 against tab 26 in handle 12 when slide 16 is in its fully forward position.

To improve the slidability of slide 16 within handle cavity 82, slide 16 is kept from contacting inner walls 48 and 58 of handle 12 when the slide is moved by an operator of the scalpel. Tab 40 and the top edge, 52, of slide half 14b form slot, 54, which is adapted to slidably engage the lower defining portion, 56, (FIG. 1) of channel 34 on the inside, 58, of side 10b. Further, notch, 70, in end piece, 72, of slide half 14b of slide 16 is adapted to slidably engage flange, 74, in side 10a of handle 12, thereby guiding tab 40 which is also formed in end piece 72, in channel 34. The upper portion of slide 16 is thereby guided along the inside of handle 12. Additionally, raised portion, 60, (FIG. 1) and flange, 62, of side 10a of handle 12 cooperate to form channel 80 (FIG. 3e) which slidably engages tabs, 64a and 64b, of lower portion, 66, of slide half 14b of slide 16, thereby guiding the lower portion of slide 16 along the inside of handle 12.

Tolerances and materials are selected such that the scalpel is stable in its operating or deployed mode yet is easily retracted. For surgical or other medical uses, materials must conform to Food and Drug Administration standards. For example, scalpels must be ethylene oxide or gamma-ray sterilizable, or autoclavable. It is anticipated that the slide and handle portions of the present scalpel will chosen for their moldability and for their relative coefficients of expansion and friction such that accurate tolerances can be maintained for operating stability, while maintaining ready relative motion and freedom from binding.

The foregoing description of the invention has been presented for purposes of illustration and description and is not intended to be exhaustive or to limit the invention to the precise form disclosed, and obviously many modifications and variations are possible in light of the above teaching. For example, it would be apparent to one having ordinary skill in the surgical arts after carefully studying the present disclosure that the retractable knife of the present may be fabricated to accommodate either right- or left-handed operators. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A surgical scalpel having a spring-actuated retractable blade, comprising in combination:

(a) an elongated handle having a first side and a second side, a first elongated cavity within said handle extending over a long dimension thereof and opening to the outside at both a forward end and a rearward end, and a tab extending into the first cavity perpendicular to the long dimension thereof and located toward the rearward end of said handle, the first side having an elongated window therethrough along the long dimension of said handle and located toward the forward end thereof and a second window therethrough disposed toward the rearward end of said handle, the first side further having a first tab extending into the first cavity and located in the vicinity of the edge of the elongated window closest to the rearward end of said handle and a second tab extending into the first cavity between the second window and the rearward end of said handle; the second side having an interior elongated slot therein which terminates before reaching the forward end of said handle and which opens to the outside of said handle at the rearward end thereof;

(b) a cutting blade;

(c) an elongated slide having a first end and a second end adapted to slidably move longitudinally through the first cavity in said handle and to receive said cutting blade in a region of the first end thereof; a digit-engaging portion adapted to be engaged by and actuated by a digit through the elongated window; a raised, deformable latch in a region of the second end on the side thereof of the digit-engaging portion for engaging either of the first or second tabs in said handle; and a tab adapted to move within the slot in the second side of said handle, said slide engaging and being reversibly immobilized by the tab extending into the first cavity of said handle when located in its rearwardmost position in said handle; and (d) a coil spring disposed within the interior elongated slot in the second side of said handle and adapted to continuously contact the tab of said slide, thereby providing a force on said slide directed toward the rearward end of said handle.

2. The surgical scalpel having a spring-actuated retractable blade as described in claim 1, wherein the first side further has a third window therethrough between the second window and the rearward end of said handle and a third tab extending into the first cavity and disposed between the third window and the rearward end of said handle, such that the deformable latch portion of said slide can engage the third tab in said handle, whereby said handle can receive a longer slide.

3. The surgical scalpel having a spring-actuated retractable blade as described in claim 1, further comprising means for reducing contact between said slide and the first side and the second side of said handle when said slide is moved through said handle.

4. The surgical scalpel having a spring-actuated retractable blade as described in claim 3, wherein said means for reducing contact between said slide and the first side and the second side of said handle includes a second cavity coextensive with the first cavity and disposed on a side of the first cavity perpendicular to the long dimension thereof and adapted to receive a portion of said slide and guide said slide within the first cavity when said slide is moved therethrough.

5. The surgical scalpel having a spring-actuated retractable blade as described in claim 1, wherein said cutting blade can be replaced on said slide.

6. The surgical scalpel having a spring-actuated retractable blade as described in claim 1, wherein the shape and thickness of the first side in the region of the elongated window is chosen such that a user of said surgical scalpel cannot accidentally depress the raised, deformable latch member of said slide through the elongated window when said cutting blade is in its extended and locked position.

7. A surgical scalpel having a spring-actuated retractable blade, comprising in combination:

(a) an elongated handle having a first side having a first interior recessed surface and a second side having a second interior recessed surface, the first interior surface and the second interior surface together forming an elongated cavity within said handle extending over a long dimension thereof and opening to the outside at both a forward end and a rearward end of said elongated handle, the first side further having a first window, a second window and a third window therethrough disposed along the first side, the first window being elongated along the long dimension of said handle and being closest to the forward end thereof and the third window being closest to the rearward end of said handle, and a tab which extends into the cavity, the second side having an interior elongated slot therein which terminates before reaching the forward end of said handle and which opens at the rearward end thereof, the first side further comprising a first tab extending into the cavity between the first window and the second window, a second tab extending into the cavity between the second window and the third window, and a third tab extending into the cavity between the third window and the rearward end of said handle;

(b) a cutting blade;

(c) an elongated slide having a first end and a second end and adapted to slidably move longitudinally through the cavity in said handle and to receive said cutting blade in a region of the first end thereof, having a digit-engaging portion adapted to be engaged by and actuated by a digit through the first window, having a raised, deformable latch in the region of the second end on the side thereof of the digit-engaging portion for engaging any of the first, second or third tabs in said handle, and having a tab adapted to move within the slot in the second side of said handle; and (d) a coil spring located within the interior slot in the second side of said handle and adapted to continuously contact the tab of said slide, thereby providing a force on said slide directed toward the rearward end of said handle.

8. The surgical scalpel having a spring-actuated retractable blade as described in claim 7, further comprising a tab extending into the first cavity of said handle perpendicular to the long dimension thereof and located toward the rearward end of said handle, said slide engaging and being reversibly immobilized by the tab when said slide is located in its rearwardmost position in said handle.

9. The surgical scalpel having a spring-actuated retractable blade as described in claim 7, further comprising means for reducing contact between said slide and the first side and the second side of said handle when said slide is moved through said handle.

10. The surgical scalpel having a spring-actuated retractable blade as described in claim 9 wherein said means for reducing contact between said slide and the first side and the second side of said handle includes a second cavity coextensive with the elongated cavity and disposed on a side of the first cavity perpendicular to the long dimension thereof and adapted to receive a portion of said slide and guide said slide within the elongated cavity when said slide is moved therethrough.

11. The surgical scalpel having a spring-actuated retractable blade as described in claim 7, wherein said cutting blade can be replaced on said slide.

12. A surgical scalpel having a spring-actuated retractable blade, comprising in combination:

(a) an elongated handle having a first side and a second side, a first elongated cavity within said handle extending over a long dimension thereof and opening to the outside at both a forward end and a rearward end, the first side having an elongated window therethrough along the long dimension of said handle and located toward the forward end thereof and a second window therethrough disposed toward the rearward end of said handle, the first side further having a first tab extending into the first cavity and located in the vicinity of the edge of the elongated window closest to the rearward end of said handle and a second tab extending into the first cavity between the second window and the rearward end of said handle; the second side having an interior elongated slot therein which terminates before reaching the forward end of said handle and which opens to the outside of said handle at the rearward end thereof;

(b) a cutting blade;

(c) an elongated slide having a first end and a second end adapted to slidably move longitudinally through the first cavity in said handle and to receive said cutting blade in a region of the first end thereof; a digit-engaging portion adapted to be engaged by and actuated by a digit through the elongated window; a raised, deformable latch in a region of the second end on the side thereof of the digit-engaging portion for engaging either of the first or second tabs in said handle; and a tab adapted to move within the slot in the second side of said handle;

(d) a tab extending into the first cavity perpendicular to the long dimension and located toward the rearward end of the handle for engaging and reversibly immobilizing said slide when said slide is located in its rearwardmost position in said handle; and (e) means for providing a force on said slide directed toward the rearward end of said handle.

13. The surgical scalpel having a spring-actuated retractable blade as described in claim 12 wherein said means for providing a force on said slide directed toward the rearward end of said handle comprises a coil spring disposed within the interior elongated slot in the second side of said handle and adapted to continuously contact the tab of said slide.

14. The surgical scalpel having a spring-actuated retractable blade as described in claim 12, wherein said means for engaging and reversibly immobilizing said slide when said slide is located in its rearwardmost position in said handle includes a tab extending into the first cavity perpendicular to the long dimension thereof and located toward the rearward end of said handle such that said slide engages and is reversibly immobilized by the tab when said slide is located in its rearwardmost position in said handle.

15. The surgical scalpel having a spring-actuated retractable blade as described in claim 12 wherein the first side further has a third window therethrough between the second window and the rearward end of said handle and a third tab extending into the first cavity and disposed between the at least one third window and the rearward end of said handle, such that the deformable latch portion of said slide can engage the at least one third tab in said handle, whereby said handle can receive a longer slide.

16. The surgical scalpel having a spring-actuated retractable blade as described in claim 12 further comprising means for reducing contact between said slide and the first side and the second side of said handle when said slide is moved through said handle.

17. The surgical scalpel having a spring-actuated retractable blade as described in claim 16 wherein said means for reducing contact between said slide and the first side and the second side of said handle includes a second cavity coextensive with the first cavity and disposed on a side of the first cavity perpendicular to the long dimension thereof and adapted to receive a portion of said slide and guide said slide within the first cavity when said slide is moved therethrough.

18. The surgical scalpel having a spring-actuated retractable blade as described in claim 12 wherein said cutting blade can be replaced on said slide.

* * * * *